United States Patent [19]
Sato et al.

[11] Patent Number: 6,121,025
[45] Date of Patent: Sep. 19, 2000

[54] PROCESS FOR PRODUCING OPTICALLY ACTIVE 3-QUINUCLIDINOL DERIVATIVES

[75] Inventors: Eiji Sato; Kanehiko Enomoto, both of Hiroshima, Japan

[73] Assignee: Mitsubishi Rayon Co., Ltd., Tokyo, Japan

[21] Appl. No.: 09/284,966

[22] PCT Filed: Nov. 4, 1997

[86] PCT No.: PCT/JP97/04009

§ 371 Date: May 5, 1999

§ 102(e) Date: May 5, 1999

[87] PCT Pub. No.: WO98/20152

PCT Pub. Date: May 14, 1998

[30] Foreign Application Priority Data

Nov. 5, 1996 [JP] Japan .................................. 8-292934

[51] Int. Cl.[7] .............................. C12P 17/12; C12P 17/10
[52] U.S. Cl. .......................... 435/122; 435/170; 435/171; 435/196; 435/198; 435/220; 435/224; 435/225; 435/913; 435/917; 435/918; 435/921; 435/939; 435/280; 435/121
[58] Field of Search ..................... 435/119, 126, 435/280, 121, 122, 170, 171, 196, 913, 917, 918, 921, 939, 198, 220, 224, 225

[56] References Cited

U.S. PATENT DOCUMENTS 3,997,543 12/1976 Sokolovsky et al. .
5,215,918 6/1993 Muchmore .

OTHER PUBLICATIONS

Chemical Abstracts, vol. 97, No. 15, AN 122771a, Oct. 11, 1982.
Chemical Abstracts, vol. 79, No. 5, AN27085z, Aug. 6, 1973.

*Primary Examiner*—Herbert J. Lilling
*Attorney, Agent, or Firm*—Oblon, Spivak, McClelland, Maier & Neustadt, P.C.

[57] ABSTRACT

The present invention relates to a process for producing optically active 3-quinuclidinol or derivatives, wherein a racemic 3-quinuclidinol ester represented by the general formula (I):

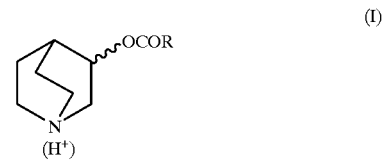

wherein R represents a straight-chain or branched alkyl group, and ($H^+$) represents that said ester may be in the form of a salt formed with a mineral acid or an organic acid, is reacted with a microorganism belonging to the genus Aspergillus, Rhizopus, Candida or Pseudomonas having the ability to asymmetrically hydrolyze said ester linkage, a culture of said microorganism, a treated material from said microorganism, an enzyme produced by said microorganism, or an enzyme derived from swine or cattle.

According to the present invention, there is provided a process for easily producing optically active 3-quinuclidinol derivatives which are important synthetic intermediates for pharmaceutical preparations etc.

4 Claims, No Drawings

PROCESS FOR PRODUCING OPTICALLY ACTIVE 3-QUINUCLIDINOL DERIVATIVES

TECHNICAL FIELD

The present invention relates to a process for producing optically active 3-quinuclidinol derivatives which are very useful compounds as starting materials or intermediates for pharmaceutical preparations, agrochemicals etc.

BACKGROUND ART

Processes for synthesizing racemic 3-quinuclidinol derivatives are widely known according to e.g. Zhur. Obshchi. Khim., 30, 163–71 (1960), Helv. 40, 2107–85 (1957), and J. Am. Chem. Soc. 74, 2215–8 (1952).

On the other hand, processes for synthesizing optically active 3-quinuclidinol derivatives are known as described in e.g. Acta. Pharm. Suec., 16, 281–3 (1979), U.S. Pat. No. 3,997,543, Life sic. 21, 1293–1302 (1977) and U.S. Pat. No. 5,215,918.

The process described in Acta. Pharm. Suec., 16, 281–3 (1979) is a process in which optically active 3-quinuclidinol derivatives are derived by a preferential crystallization method using optically active tartaric acid as a resolution agent, and this prior art process requires the cumbersome procedure that e.g. recrystallization should be repeated several or more times to raise optical purity.

Further, the processes described in U.S. Pat. No. 3,997,543, Life sic. 21, 1293–1302 (1977) and U.S. Pat. No. 5,215,918 report processes for obtaining optically active 3-quinuclidinol derivatives by asymmetrically hydrolyzing lower fatty esters of 3-quinuclidinol with an enzyme. However, the enzyme used in U.S. Pat. No. 3,997,543 and Life sic. 21, 1293–1302 (1977) is a butyryl choline esterase only, and the enzyme used in U.S. Pat. No. 5,215,918 is an only specific enzyme (subtilisin) produced by the genus Bacillus, and thus the type of enzyme used in any of these literatures is limited so these cannot be said to be general processes. There are still not known any other processes for producing optically active 3-quinuclidinol derivatives by means of general enzymes.

Accordingly, the useful process for synthesizing optically active 3-quinuclidinol derivatives, provided by the present invention, has been desired.

DISCLOSURE OF THE INVENTION

Accordingly, the object of the present invention is to provide a process for easily producing optically active 3-quinuclidinol derivatives which are useful intermediates and starting materials for optically active pharmaceutical preparations and optically active agrochemicals.

As a result of their eager study on the process for synthesizing optically active 3-quinuclidinol derivatives, the present inventors found selected enzymes and microorganisms having an activity of optico-selectively hydrolyzing a racemic ester of 3-quinuclidinol, and the present invention was thereby completed.

That is, the present invention relates to a process for producing optically active 3-quinuclidinol or a salt thereof, wherein a racemic 3-quinuclidinol ester represented by the general formula (I):

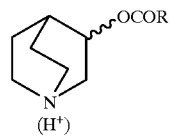

wherein R represents a straight-chain or branched alkyl group, and ($H^+$) represents that said ester may be in the form of a salt formed with a mineral acid or an organic acid, is reacted with a microorganism belonging to the genus Aspergillus, Rhizopus, Candida or Pseudomonas having the ability to asymmetrically hydrolyze said ester linkage, a culture of said microorganism, a treated material from said microorganism, an enzyme produced by said microorganism, or an enzyme derived from swine or cattle.

Further, the present invention relates to a process for producing optically active 3-quinuclidinol ester or a salt thereof, wherein a racemic 3-quinuclidinol ester represented by the general formula (I):

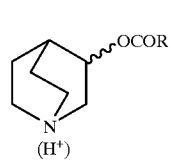

wherein R represents a straight-chain or branched alkyl group, and ($H^+$) represents that said ester may be in the form of a salt formed with a mineral acid or an organic acid, is reacted with a microorganism belonging to the genus Aspergillus, Rhizopus, Candida or Pseudomonas having the ability to asymmetrically hydrolyze said ester linkage, a culture of said microorganism, a treated material from said microorganism, an enzyme produced by said microorganism, or an enzyme derived from swine or cattle.

Hereinafter, the present invention is described in detail.

The straight-chain or branched alkyl group R in the starting material in the process of the present invention, i.e. in the racemic ester of 3-quinuclidinol represented by the general formula (I), is not particularly limited insofar as it is an alkyl group containing 1 to 10 carbon atoms, and specific examples include methyl, ethyl, propyl, isopropyl, butyl, isobutyl, tert-butyl, valel, isovalel, pival, hexyl, pentyl, octyl, decyl etc. Among those enumerated above, alkyl groups containing 1 to 5 carbon atoms are particularly preferable. Further, these may carry a substituted or unsubstituted phenyl group. As the substituent group, there may be mentioned an alkyl group, acyl group, halogen group and hydroxyl group.

The portion of the nitrogen atom in the racemic ester of 3-quinuclidinol may intentionally have formed a salt with an organic acid or a mineral acid or the like as shown in the general formula (I). As the specific mineral acid salt, there may be mentioned hydrochloride, hydrobromate, sulfate, nitrate etc. As the organic acid salt, there may be mentioned aliphatic organic acid salts such as acetate, propionate, butyrate, fumarate, malonate and oxalate, as well as aromatic organic acid salts such as benzoate etc.

Hereinafter, the specific process of the present invention is described.

The starting material i.e. the racemic 3-quinuclidinol ester can be easily synthesized in a method known in the art as described above. That is, racemic 3-quinuclidinol is first synthesized from isonicotinate, bromoacetate etc. as the starting material (J. Am. Chem. Soc. 74, 2215–8 (1952)) and then reacted with an organic acid chloride or organic acid anhydride etc. whereby the desired ester can be synthesized.

The microorganisms belonging to the genera Aspergillus, Rhizopus, Candida and Pseudomonas producing an enzyme having the ability to produce optically active 3-quinuclidinol and/or enantiomer esters thereof by asymmetric hydrolysis of the ester linkages in racemic 3-quinuclidinol esters represented by the general formula (I) used in the present invention are not particularly limited, and specific examples include *Aspergillus oryzae, Aspergillus melleus, Aspergillus sojae, Aspergillus niger, Aspergillus saitoi, Candida antarctica* and Pseudomonas sp. MR2301 strain FERM BP4870.

A wide variety of lipases, proteases and esterases can be used as the enzyme produced by the microorganisms of the genera Aspergillus, Rhizopus, Candida and Pseudomonas capable of asymmetric hydrolysis used in the present invention. Among these enzymes, those commercially available are e.g. Amano Seiyaku Lipase A6 (derived from the genus Aspergillus), Amano Seiyaku Lipase AP4 (derived from the genus Aspergillus), Amano Seiyaku Lipase AP6 (derived from the genus Aspergillus), SIGMA Acylase I (derived from *Aspergillus melleus*), SIGMA Protease Type II (derived from *Aspergillus oryzae*), SIGMA Protease Type XIII (derived from *Aspergillus saitoi*), SIGMA Protease (Newlase) Type XVIII (derived from the genus Rhizopus), SIGMA Protease Type XIX (derived from *Aspergillus sojae*), SIGMA Protease Type XXIII (derived from *Aspergillus oryzae*), Fluka Lipase (derived from *Candida antarctica*), Nagase Seikagaku Kogyo Denazyme AP (derived from *Aspergillus oryzae*), Nagase Seikagaku Kogyo Denapsin 10P (derived from *Aspergillus niger*), NOVO Flavourzyme MG (derived from *Aspergillus oryzae*) etc.

Further, the enzyme derived from swine or cattle capable of asymmetric hydrolysis used in the present invention is not particularly limited, and it is possible to use a wide variety of lipases, proteases and esterases. The enzyme derived from swine or cattle includes SIGMA Protease Type I (derived from bovine spleen), SIGMA Acylase I (derived from porcine kidney), SIGMA Trypsin (Type II) (derived from porcine spleen).

When the ester hydrolase described above is subjected to the reaction in the process of the present invention, the mode of its use is not particularly limited insofar as said enzyme exhibits the activity, and the enzyme can be used not only in a purified form but also in a crude form containing additives added for stabilizing the enzyme. Further, if the microorganism having the ability to produce the ester hydrolase as described above is subjected to the reaction, the culture liquid itself obtained by culturing the microorganism, or the microorganism harvested from the culture by centrifugation etc., or the treated material can be used. If the enzyme is produced extracellularly, the culture after removing the microorganism by centrifugation can be used as such, but it is more effective to conduct the operation of concentration and purification by ammonium sulfate treatment etc. The treated material of the microoganism includes a microorganism treated with acetone, toluene etc., a lyophilized microorganism, a disrupted microorganism, a cell-free extract from the disrupted microorganism, and a crude enzyme solution extracted from these materials. Further, the enzyme or the microorganism can be immobilized for use so that their recovery and reuse can be facilitated after the reaction. For example, they can be immobilized by inclusion into cross-linked acrylamide gel or physically or chemically immobilized on solid carriers such as ion-exchange resin, diatomaceous earth.

The enzyme derived from the microorganism used in the present invention is obtained by culturing the microorganism producing said enzyme, and the microorganism can be cultured in a liquid or solid medium. As this medium, there is used a medium suitably containing ingredients such as carbon sources, nitrogen sources, vitamins, minerals etc. which can be assimilated by said microorganism. To improve the hydrolysis ability of the microorganism, a small amount of inducers etc. can also be added to the medium. Culture is performed at the temperature and pH at which the microorganism can grow, preferably under the optimum culture conditions for the strain used. To promote growth of the microorganism, stirring under aeration is conducted in some cases.

For optico-selective hydrolysis of the racemic 3-quinuclidinol ester, the racemic 3-quinuclidinol ester serving as the substrate is dissolved or suspended in a reaction solvent. Then, the enzyme, the microorganism, the culture of the microorganism or the treated material from the microorganism, which act as a catalyst, is added thereto, and while controlling the reaction temperature and the pH of the reaction solution if necessary, the reaction is continued until approximately half of the 3-quinuclidinol esters are hydrolyzed. Depending on the case, the reaction may be terminated at an initial stage or may proceed excessively.

The concentration of the substrate during the reaction is not particularly limited in the range of 0.1 to 70% by weight, but in consideration of the solubility, productivity etc. of the racemic 3-quinuclidinol ester as the substrate, the reaction is conducted using the substrate preferably in the range of 5 to 50% by weight. The substrate can be added thereto as such or in the form of a solution in an organic solvent.

As described above, the portion of the nitrogen atom in the 3-quinuclidinol derivative may have formed a salt with an organic acid or a mineral acid or the like.

As regards the reaction time, conditions are selected such that the reaction is finished usually for 1 hour to 1 week, preferably for 1 to 72 hours.

The reaction pH depends on the optimum pH of the microbial enzyme used, but it is preferable that the reaction is conducted usually in the range of pH 4 to 11, particularly in the range of pH 6 to 9.5 in order to prevent the reduction of optical purity caused by chemical hydrolysis. As the reaction proceeds, the pH of the reaction solution is decreased due to the carboxylic acid formed, and in this case, the progress of the reaction is often promoted by maintaining the optimum pH with a suitable neutralizing agent such as sodium hydroxide, potassium hydroxide etc. The reaction temperature is preferably in the range of 5 to 70° C., more preferably 10 to 60° C.

Usually, the reaction solvent makes use of aqueous media such as deionized water, buffers etc., but the reaction can also be effected even in a system containing an organic solvent. For example, it is possible to suitably use organic solvents e.g. alcohols such as methanol, ethanol, propanol, isopropanol, butanol, isobutanol, tert-butanol, tert-amyl alcohol etc., ethers such as diethyl ether, isopropyl ether, dioxane etc., ketones such as acetone, methyl ethyl ketone, methyl isobutyl ketone etc., aromatic and hydrocarbon solvents such as hexane, octane, benzene, toluene etc. The reaction can also be effected in a 2-phase system in which the organic solvent is added in such excess as not to be dissolved in water.

There are many cases where selectivity, transformation, yield etc. are improved by allowing the organic solvent to be present in the reaction system.

The substrate concentration, reaction temperature, reaction solvent, reaction time, oxygen concentration and other reaction conditions described above are suitably selected in consideration of the reaction yield, optical yield etc. under such conditions, in order to attain the maximum amount of the desired optically specific compounds to be recovered.

According to the reaction described above, a reaction solution containing optically active 3-quinuclidinol whose ester linkage was asymmetrically hydrolyzed and its enantiomer (unreacted enantiomer ester), that is, the optically active 3-quinuclidinol ester which was not hydrolyzed, can be obtained from the racemic 3-quinuclidinol ester.

Isolation of the optically active 3-quinuclidinol or the optically active 3-quinuclidinol ester (unreacted enantiomer ester) from the resulting reaction solution can make use of any separation techniques such as distillation, extraction, separation on columns, recrystallization etc. known in the art.

The optically active 3-quinuclidinol ester (unreacted enantiomer ester) can be obtained for example by removing the enzyme or the microorganism used as the catalyst by operations such as centrifugation, filtration etc., then adjusting the pH, and extracting it with a solvent such as hexane, chloroform or ethyl acetate.

On the other hand, the hydrolyzed optically active 3-quinuclidinol can be obtained for example by concentrating the extracted residue and further re-crystallizing it from a solvent such as benzene, toluene, acetone etc.

Prior to separation of the optically active 3-quinuclidinol from its enantiomer ester, a part or the whole of the reaction solvent may be removed by distillation etc. depending on the amount and type of the organic solvent contained in the reaction solvent, and then a suitable organic solvent may be added thereto depending on the case.

The resulting optically active 3-quinuclidinol ester (unreacted enantiomer ester) can be hydrolyzed in a usual manner whereby the ester while maintaining the optical activity can be converted into 3-quinuclidinol. Further, the optically active 3-quinuclidinol can be esterified in a usual manner whereby the 3-quinuclidinol while maintaining the optical activity can be converted into the 3-quinuclidinol ester. Accordingly, the optically active 3-quinuclidinol derivatives with arbitrary configuration can be obtained.

These optically active 3-quinuclidinol derivatives contain tertiary amines, so their amine salts can be formed in a usual manner.

BEST MODE FOR CARRYING OUT THE INVENTION

Hereinafter, the present invention is described in more detail by reference to Reference Examples and typical Examples, but these examples are not intended to limit the scope of the present invention. [Reference Example 1] Synthesis of racemic 3-quinuclidinol ester.
1) Synthesis of 3-quinuclidinyl acetate 8.1 g of acetic anhydride was dropped slowly to 10 g of 3-quinuclidinol (Tokyo Kasei Kogyo K. K.), and the mixture was stirred for 20 hours at room temperature to synthesize 3-quinuclidinyl acetate.
2) Synthesis of 3-quinuclidinyl butyrate 12.5 g of butyric anhydride was dropped slowly to 10 g of 3-quinuclidinol, and the mixture was stirred for 20 hours at room temperature to synthesize 3-quinuclidinyl butyrate.

EXAMPLE 1

10.0 g of 3-quinuclidinyl butyrate was dissolved in 150 ml of 50 mM phosphate buffer (pH 7), then 5.0 g of Denazyme AP from Nagase Seikagaku Kogyo was added thereto, and the reaction was initiated at 30° C. while maintaining pH 7.0 with 0.5 N NaOH. When the approximately theoretical amount of the alkali was added, the reaction was terminated, and hexane was added thereto, and sodium carbonate was added thereto under stirring, thus making the pH of the aqueous phase alkaline and the liquid was separated. The hexane layer was concentrated to give 2.5 g of (R) 3-quinuclidinyl butyrate. Specific rotation $[\alpha]^{24}_D = +34$ (neat).

The resulting (R) 3-quinuclidinyl butyrate was hydrolyzed with water-NaOH and then recrystallized from toluene to give (R)-quinuclidinol. Specific rotation $[\alpha]^{24}_D = -45$ (1N HCl).

The resulting (R) 3-quinuclidinyl butyrate was dissolved in a 5-fold excess volume of methanol, and 3-fold molar equivalents of conc. hydrochloric acid were added thereto and the mixture was refluxed for 5 hours. The reaction solution was concentrated into dryness to give (R) 3-quinuclidinol hydrochloride quantitatively.

The (S) 3-quinuclidinol hydrolyzed by the enzyme reaction was recovered by removing water and the enzyme followed by recrystallization from toluene in a similar manner. Specific rotation $[\alpha]^{24}_D = +37$ (1N HCl).

EXAMPLE 2

3-Quinuclidinyl butyrate was dissolved at 5% by weight in 500 mM phosphate buffer (pH 7), and an enzyme shown in Table 2 was added thereto suitably in the range of 1 to 5% by weight and allowed to react at 30° C. for 20 hours. The concentration and optical purity of the 3-quinuclidinol were determined by gas chromatography (column: CP-Chirasil DEX CB 0.25×25 M, from Chrom Back). The results are collectively shown in Table 1.

TABLE 1

Results of Asymmetric Hydrolysis of 3-Quinuclidinyl Butyrate

| Enzymes | concentration of 3-quinuclidinol | optical purity of 3-quinuclidinol |
| --- | --- | --- |
| SIGMA Acylase I: Aspergillus melleus | 1.0 wt-% | 100% ee (S)-body |
| SIGMA Protease Type I: Bovine Pancreas | 1.1 wt-% | 55% ee (S)-body |
| SIGMA Protease Type II: Aspergillus oryzae | 1.1 wt-% | 80% ee (S)-body |
| SIGMA Protease (Newlase) Type XVIII: Rhizopus species | 0.8 wt-% | 100% ee (S)-body |
| SIGMA Protease Type XIX: Aspergillus sojae | 0.9 wt-% | 80% ee (S)-body |
| SIGMA Protease Type XXIII: Aspergillus oryzae | 1.6 wt-% | 29% ee (S)-body |
| SIGMA Trypsin Type II: Porcine Pancreas | 1.5 wt-% | 30% ee (S)-body |
| Fluka Lipase: Candida antarctica | 1.6 wt-% | 22% ee (S)-body |
| NOVO Flavourzyme MG: Aspergillus oryzae | 1.1 wt-% | 70% ee (S)-body |

EXAMPLE 3

3-Quinuclidinyl acetate was dissolved at 5% by weight in 500 mM phosphate buffer (pH 7), and an enzyme shown in Table 2 was added thereto suitably in the range of 1 to 5% by weight and allowed to react at 30° C. for 20 hours. The concentration and optical purity of the 3-quinuclidinol were determined by gas chromatography (column: CP-Chirasil DEX CB 0.25×25 M, from Chrom Back). The results are collectively shown in Table 2.

TABLE 2

Results of Asymmetric Hydrolysis of 3-Quinuclidinyl Acetate

| Enzymes | concentration of 3-quinuclidinol | optical purity of 3-quinuclidinol |
|---|---|---|
| Amano Seiyaku Lipase A6 | 2.1 weight-% | 16% ee (S)-body |
| Amano Seiyaku Lipase AP4 | 1.8 weight-% | 23% ee (S)-body |
| Amano Seiyaku Lipase AP6 | 2.5 weight-% | 13% ee (S)-body |
| SIGMA Acylase I: *Porcine Kidney* | 0.9 weight-% | 75% ee (S)-body |
| SIGMA Protease Type II: *Aspergillus oryzae* | 0.5 weight-% | 100% ee (S)-body |
| SIGMA Protease Type XIII: *Aspergillus saitoi* | 0.8 weight-% | 51% ee (S)-body |
| SIGMA Protease Type XXIII: *Aspergillus oryzae* | 0.9 weight-% | 75% ee (S)-body |
| Nagase Seikagaku Kogyo Denazyme AP: *Aspergillus oryzae* | 0.7 weight-% | 65% ee (S)-body |
| Nagase Seikagaku Kogyo Denapsin 10P: *Aspergillus niger* | 0.7 weight-% | 50% ee (S)-body |

EXAMPLE 4

Pseudomonas sp. MR2301 strain FERM BP4870 was inoculated into 50 ml LB medium (1 weight-% polypeptone, 0.5 weight-% yeast extract, 0.5 weight-% NaCl) containing 0.1 weight-% lactamide and cultured at 30° C. for 48 hours with shaking. After culturing was finished, the culture was centrifuged, and the whole of the microorganism thus obtained was washed with deionized water and suspended in 50 ml of 500 mM phosphate buffer (pH 7.0). 2.5 g of racemic 3-quinuclidinyl acetate was added to this microbial suspension and allowed to react at 30° C. for 20 hours. The presence of 3-quinuclidinol at a concentration of 1.3 weight-% with an optical purity of 31% ee (S)-body was confirmed by analyzing the reaction solution by gas chromatography (column: CP-Chirasil DEX CB, from Chrom Back).

Industrial Applicability

According to the present invention, there is provided a process for easily producing optically active 3-quinuclidinol derivatives which are important synthetic intermediates for pharmaceutical preparations etc.

What is claimed is:

1. A process for producing optically active 3-quinuclidinol or a salt thereof, wherein a racemic 3-quinuclidinol ester represented by the general formula (I):

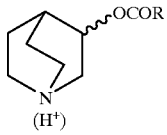

(I)

wherein R represents a straight-chain or branched alkyl group containing 1 to 10 carbon atoms, and (H+) represents that said ester may be in the form of a salt formed with a mineral acid or an organic acid, is reacted with a microorganism having the ability to asymmetrically hydrolyze said ester linkage, wherein said microorganism is selected from the group consisting of Rhizopus sp., *Aspergillus oryzae, Aspergillus melleus, Aspergillus sojae, Aspergillus niger, Aspergillus saitoi, Candida antarctica,* and Pseudomonas sp. MR2301 strain FERM BP4870, a culture of said microorganism, a treated material from said microorganism, or an enzyme produced by said microorganism, wherein said treated material from said microorganism is selected from the group consisting of the microorganism treated with acetone, the microorganism treated with toluene, the lyophilized microorganism, the disrupted microorganism, a cell-free extract from the microorganism, and a crude enzyme solution extracted from the microorganism, and wherein said enzyme is a lipase, protease or esterase.

2. A process for producing optically active 3-quinuclidinol or a salt thereof, wherein a racemic 3-quinuclidinol ester represented by the general formula (I):

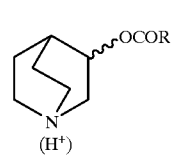

(I)

wherein R represents a straight-chain or branched alkyl group containing 1 to 10 carbon atoms, and (H+) represents that said ester may be in the form of a salt formed with a mineral acid or an organic acid, and is reacted with a protease, acylase or trypsin derived from swine or cattle having the ability to asymmetrically hydrolyze said ester linkage.

3. A process for producing optically active 3-quinuclidinol ester or a salt thereof, wherein a racemic 3-quinuclidinol ester represented by the general formula (I):

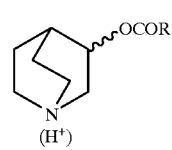

(I)

wherein R represents a straight-chain or branched alkyl group containing 1 to 10 carbon atoms, and (H+) represents that said ester may be in the form of a salt formed with a mineral acid or an organic acid, is reacted with a microorganism having the ability to asymmetrically hydrolyze said ester linkage, wherein said microorganism is selected from the group consisting of Rhizopus sp., *Aspergillus oryzae, Aspergillus melleus, Aspergillus sojae, Aspergillus niger, Aspergillus saitoi, Candida antarctica,* and Pseudomonas sp. MR2301 strain FERM BP4870, a culture of said microorganism, a treated material from said microorganism, or an enzyme produced by said microorganism, wherein said treated material from said microorganism is selected from the group consisting of the microorganism treated with acetone, the microorganism treated with toluene, the lyophilized microorganism, the disrupted microorganism, a cell-free extract from the microorganism, and a crude enzyme solution extracted from the microorganism, and wherein said enzyme is a lipase, protease or esterase.

4. A process for producing optically active 3-quinuclidinol ester or a salt thereof, wherein a racemic 3-quinuclidinol ester represented by the general formula (I):

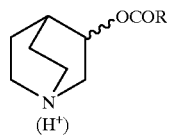
(I)
wherein R represents a straight-chain or branched alkyl group containing 1 to 10 carbon atoms, and (H$^+$) represents that said ester may be in the form of a salt formed with a mineral acid or an organic acid, and is reacted with a protease, acylase or trypsin derived from swine or cattle having the ability to asymmetrically hydrolyze said ester linkage.
* * * * *